(12) United States Patent
Wouters et al.

(10) Patent No.: US 9,283,376 B2
(45) Date of Patent: Mar. 15, 2016

(54) INTERAURAL TIME DIFFERENCE ENHANCEMENT STRATEGY

(75) Inventors: Jan Wouters, Macquarie University (AU); Tom Francart, Macquarie Univerity (AU)

(73) Assignee: Cochlear Limited, Macquarie University, NSW (AU)

(*) Notice: Subject to any disclaimer, the term of this patent is extended or adjusted under 35 U.S.C. 154(b) by 1236 days.

(21) Appl. No.: 13/117,577

(22) Filed: May 27, 2011

(65) Prior Publication Data

US 2012/0303093 A1  Nov. 29, 2012

(51) Int. Cl.
*A61N 1/36* (2006.01)
*A61N 1/05* (2006.01)

(52) U.S. Cl.
CPC .......... *A61N 1/0541* (2013.01); *A61N 1/36032* (2013.01)

(58) Field of Classification Search
CPC ... A61N 1/08; A61N 1/36062; H04R 2225/43
USPC .................................................. 607/55–57
See application file for complete search history.

(56) References Cited

U.S. PATENT DOCUMENTS

| | | | |
|---|---|---|---|
| 5,870,481 A | 2/1999 | Dymond et al. | |
| 5,991,419 A | 11/1999 | Brander | |
| 6,349,277 B1* | 2/2002 | Kamai et al. | 704/207 |
| 7,076,072 B2 | 7/2006 | Feng et al. | |
| 7,310,558 B2 | 12/2007 | Van Hoesel | |
| 2004/0052231 A1* | 3/2004 | Ramaswamy et al. | 370/338 |
| 2005/0209657 A1 | 9/2005 | Chung et al. | |
| 2005/0261748 A1* | 11/2005 | van Dijk | 607/57 |
| 2006/0080087 A1* | 4/2006 | Vandali et al. | 704/207 |
| 2006/0287690 A1 | 12/2006 | Bouchataoui et al. | |

FOREIGN PATENT DOCUMENTS

| | | |
|---|---|---|
| WO | WO 2007/128825 A1 | 11/2007 |
| WO | WO 2008/155123 A1 | 12/2008 |
| WO | WO 2010/115227 A1 | 10/2010 |

OTHER PUBLICATIONS

Han, Xianhua et al. "Implementation of Spectral Maxima Sound Processing for Cochlear Implants by using Bark Scale Frequency Band Partition." Proceedings—23$^{rd}$ Annual Conference—IEEE/EMBS Oct 25-28, 2001.*

* cited by examiner

*Primary Examiner* — Allen Porter, Jr.

(57) ABSTRACT

Aspects of the present invention are generally directed to a modulation enhancement strategy that helps improve ITD perception by explicitly modulating the electrical stimulation signal. In an embodiment, the timing of the applied modulations is based on amplitude inflections (i.e., peaks or troughs) in the received sound signal. In an embodiment, the identified inflections (i.e., peaks or troughs) represent the most energetic portions of the signal over a particular time period (e.g., the time period prior to the inflection having a length equal to the expected fundamental period of the signal. Further, in an embodiment, the cochlear implant applies a delay to the stimulation signal to help maintain interaural timing cues. The application of this delay helps account for the traveling wave delay in the acoustic path of the opposite ear in embodiments in which the opposite ear is fitted with a hearing aid or is not fitted with a hearing device.

29 Claims, 8 Drawing Sheets

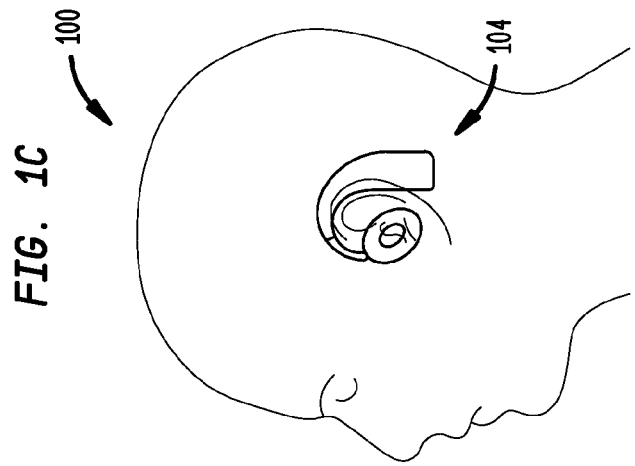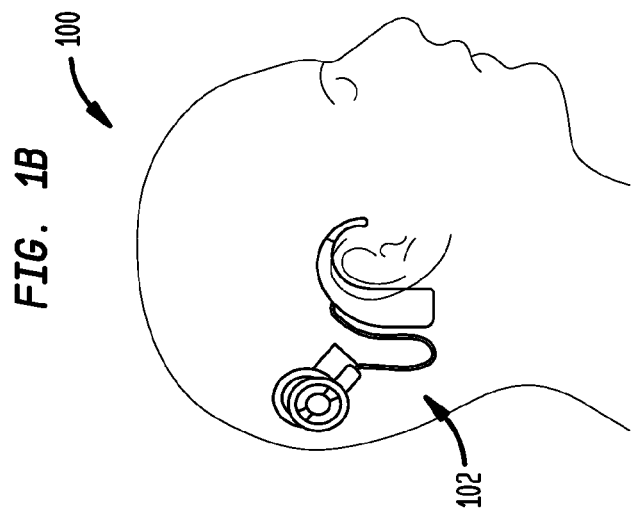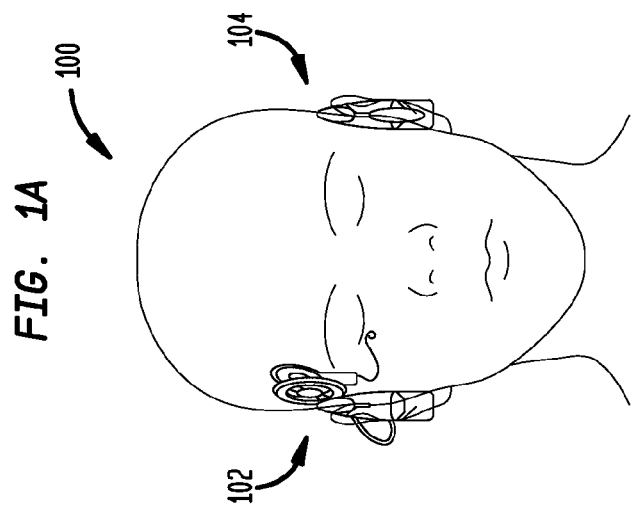

INTERAURAL TIME DIFFERENCE ENHANCEMENT STRATEGY

BACKGROUND

1. Field of the Invention

The present invention relates generally to hearing prostheses, and more particularly, to hearing prostheses that provide electrical stimulation to the auditory nerve.

2. Related Art

Hearing loss, which may be due to many different causes, is generally of two types, conductive or sensorineural. In many people who are profoundly deaf, the reason for their deafness is sensorineural hearing loss. This type of hearing loss is due absent, damaged or destroyed hairs in the cochlea that normally transduce acoustic signals into nerve impulses. Various hearing prostheses have been developed to provide individuals suffering from sensorineural hearing loss with the ability to perceive sound.

One type of hearing prosthesis, referred to as a cochlear implant, includes an electrode assembly implanted in the cochlea. Electrical stimulation signals are delivered to the auditory nerve via the electrode assembly, thereby inducing a hearing sensation in the implant recipient.

Conductive hearing loss occurs when the normal mechanical or acoustical pathways which conduct sound to the cochlea are impeded. This problem may arise, for example, as a result of damage to the ossicular chain or ear canal. Individuals suffering from conductive hearing loss frequently retain some form of residual hearing because the hairs in the cochlea are undamaged. For this reason, individuals who suffer from conductive hearing loss typically are not candidates for a conventional cochlear implant system because insertion of the electrode assembly into the cochlea may severely damage or destroy the remaining hairs in the cochlea.

Individuals with conductive hearing loss typically receive an acoustic stimulation hearing aid. Such aids can also benefit individuals with sensorineural hearing loss who have sufficient residual hearing to not be candidates for a cochlear implant. Hearing aids receive ambient sound, amplify the sound, and direct the amplified sound through the ear canal. The amplified sound reaches the cochlea and causes motion of the cochlea fluid, thereby stimulating the hairs in the cochlea.

Unfortunately, hearing aids do not benefit all individuals with conductive hearing loss. For example, some individuals are prone to chronic inflammation or infection of the ear canal. Other individuals have malformed or absent auricle(s) and/or ear canal(s) as a result of a birth defect, or as a result of a medical condition such as Treacher Collins syndrome or Microtia.

Individuals unable to benefit from hearing aids may benefit from implantable hearing prostheses that deliver mechanical energy to the recipient. In one type of implantable hearing prosthesis, referred to a "middle ear mechanical stimulation system," an implanted actuator is connected to the ossicular chain, thereby enabling direct vibration of the ossicular chain to induce an auditory response. In another type of hearing prosthesis, referred to as an "inner ear mechanical stimulation system," an implanted actuator is connected to the cochlea and operates by directly vibrating the cochlea thus causing vibrations in the perilymph.

Another type of acoustic stimulation hearing prosthesis, referred to as a bone conduction device, such as a Baha®, has an actuator implanted into the skull of the recipient. The actuator provides vibrations directly to the recipient's skull bone. These vibrations are conducted by the recipient's bony structure to the inner ear to elicit an auditory response.

Some individuals are provided a bilateral hearing system to treat sensorineural hearing loss. A bilateral hearing system refers to a system in which the individual is provided with a hearing prosthesis for both ears. For example, some individuals with bilateral sensorineural hearing loss are provided a bilateral hearing system comprising a cochlear implant for one ear and a hearing aid for the other.

SUMMARY

In one aspect of the invention, there is provided a method for delivering a stimulating signal by a cochlear implant having a plurality of electrodes, wherein the cochlear implant is attached to a first ear of a recipient, the method comprising: receiving a sound signal; filtering the received signal to obtain a first set of one or more band-pass filtered signals; determining a time instance indicative of an inflection in the received sound signal; modulating at least one of the band-pass filtered signals at the determined time instance; and delivering, via one or more of the plurality of electrodes, a stimulation signal using the modulated at least one band-pass filtered signal and a delay; wherein the delay is indicative of a difference in a time lag between receipt of the sound signal at the first ear and electrical stimulation of an auditory nerve in the first ear by the cochlear implant and a time lag between receipt of the sound signal at a second ear of the recipient and stimulation of a second auditory nerve in the second ear.

In another aspect, there is provided a cochlear implant comprising: a filter bank configured to obtain a first set of one or more band-pass filtered signals from a received sound signal; a time selector configured to determine a time instance indicative of an inflection in the received sound signal; a modulator configured to modulate at least one of the band-pass filtered signals at the determined time instance; a delay configured to delay application of electrical stimulation in accordance with the modulated band-pass filtered signal; and a plurality of electrodes configured to deliver a stimulation signal using the modulated at least one band-pass filtered signal to a first ear of a recipient; wherein the delay is indicative of a difference in a time lag between receipt of the sound signal at the first ear and electrical stimulation of an auditory nerve in the first ear by the cochlear implant and a time lag between receipt of the sound signal at a second ear of the recipient and stimulation of a second auditory nerve in the second ear.

In yet another aspect, there is provided a bilateral hearing system comprising: a hearing aid configured to be attached to a first ear of a recipient; and a cochlear implant configured to be attached to a second ear of the recipient, wherein the cochlear implant comprises: a filter bank configured to obtain a first set of one or more band-pass filtered signals from a received sound signal; a time selector configured to determine a time instance indicative of an inflection in the received sound signal; a modulator configured to modulate at least one of the band-pass filtered signals at the determined time instance; a delay configured to delay application of electrical stimulation in accordance with the modulated band-pass filtered signal; and a plurality of electrodes configured to deliver a stimulation signal using the modulated at least one band-pass filtered signal to a first ear of a recipient; and wherein the delay is indicative of a difference in a time lag between receipt of the sound signal at the first ear and electrical stimulation of an auditory nerve in the first ear by the cochlear implant and a time lag between receipt of the sound signal at a second ear of the recipient and stimulation of a second auditory nerve in the second ear.

BRIEF DESCRIPTION OF THE DRAWINGS

Illustrative embodiments of the present invention are described herein with reference to the accompanying drawings, in which:

FIG. 1A-1C are perspective views of a bilateral hearing system in which embodiments of the present invention may be implemented;

DETAILED DESCRIPTION

Recipients of a cochlear implant with residual hearing in the non-implanted ear typically can only make limited use of interaural timing cues with current cochlear implants. Depending on the location from which a sound originates, the sound can arrive earlier at one ear of an individual than the other ear. For example, if a sound originates on the left side of an individual, the sound will arrive at the left ear of the individual prior to arrival at the right ear. This difference in time between when a sound arrives at one ear versus the other is referred to as the interaural time difference (ITD). Interaural timing cues, such as the ITD, are important for sound source localization and the unmasking of speech in noise.

As will be discussed further below, an embodiment of the present invention employs a modulation enhancement strategy that helps improve ITD perception by explicitly modulating the electrical stimulation signal. In an embodiment, the timing of the modulations is determined based on an amplitude inflection (e.g., a peak) in the received sound signal that has an intensity greater than a particular percentage over a particular time period (e.g., the expected fundamental period). In one such embodiment, the timing of the modulations is based on the glottal closure instants (GCI) in a received voiced sound signal. Further, in an embodiment, the cochlear implant applies a delay to the stimulation signal to help maintain interaural timing cues. The application of this delay helps account for the traveling wave delay in the acoustic path of the opposite ear in embodiments in which the opposite ear is fitted with a hearing aid, or other acoustic hearing prosthesis, or is not fitted with a hearing device (i.e. no hearing device is attached to the ear).

FIGS. 1A-1C are perspective views of a recipient wearing a bilateral hearing system 100, in accordance with an embodiment of the present invention. FIG. 1A is front view of the recipient wearing a cochlear implant 102 on their right side and a hearing aid 104 on their left side. FIG. 1B illustrates the right side and FIG. 1C illustrates the left side of the recipient wearing bilateral hearing system 100. As will be discussed further below, cochlear implant 102 (commonly referred to as cochlear prosthetic devices, cochlear implant systems, cochlear implants, cochlear devices, and the like; simply "cochlea implant" herein) is configured to deliver electrical stimulation to the cochlea of the recipient. Hearing aid 104 is configured to deliver acoustic stimulation to the recipient. A further description of cochlear implant 102 and hearing aid 104 is provided below.

Figure 2:
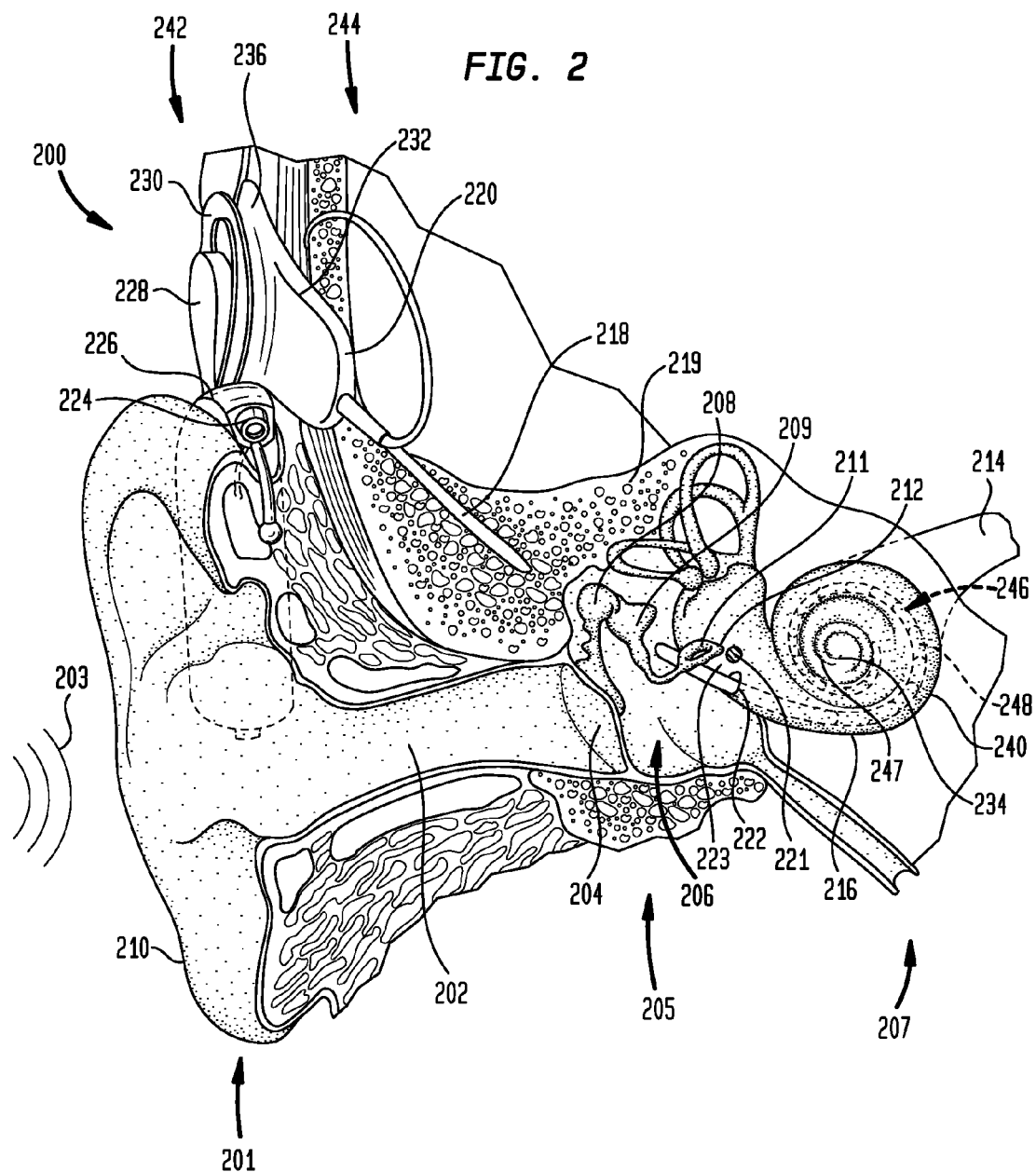
FIG. 2 is a perspective view of a cochlear implant system in which embodiments of the present invention may be implemented.
Figure 3:
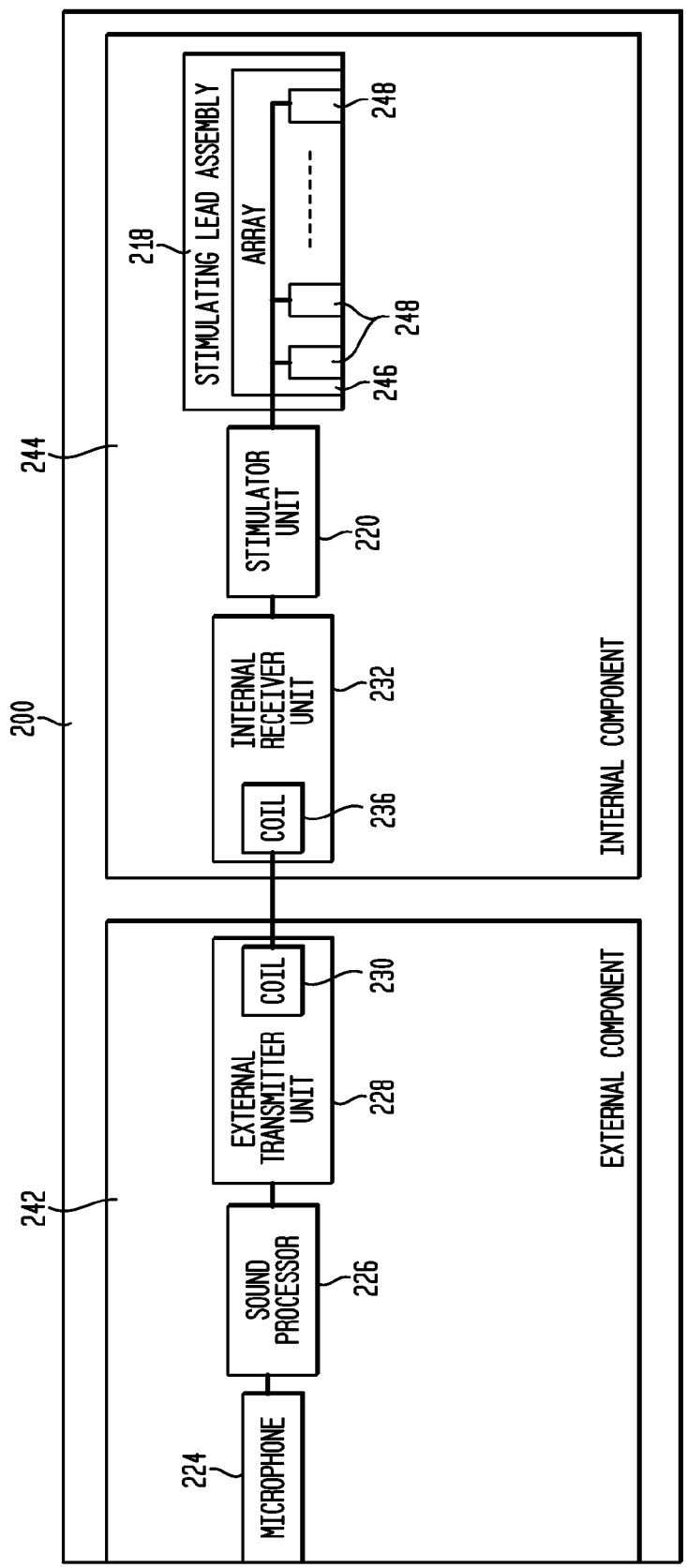
FIG. 3 is a functional block diagram of the cochlear implant system of FIG. 1, in accordance with an embodiment of the present invention.

FIG. 2 is a perspective view of an exemplary cochlear implant, referred to as cochlear implant system 200 implanted in a recipient. In an embodiment, cochlear implant 200 is used as cochlear implant 102 of FIG. 1. FIG. 3 is a functional block diagram of cochlear implant system 200. The recipient has an outer ear 201, a middle ear 205 and an inner ear 207. Components of outer ear 201, middle ear 205 and inner ear 207 are described below, followed by a description of cochlear implant 200.

In a fully functional ear, outer ear 201 comprises an auricle 210 and an ear canal 202. An acoustic pressure or sound wave 203 is collected by auricle 210 and channeled into and through ear canal 202. Disposed across the distal end of ear cannel 202 is a tympanic membrane 204 which vibrates in response to sound wave 203. This vibration is coupled to oval window or fenestra ovalis 212 through three bones of middle ear 205, collectively referred to as the ossicles 206 and comprising the malleus 208, the incus 209 and the stapes 211. Bones 208, 209 and 211 of middle ear 205 serve to filter and amplify sound wave 203, causing oval window 212 to articulate, or vibrate in response to vibration of tympanic membrane 204. This vibration sets up waves of fluid motion of the perilymph within cochlea 240. Such fluid motion, in turn, activates tiny hair cells (not shown) inside of cochlea 240. Activation of the hair cells causes appropriate nerve impulses to be generated and transferred through the spiral ganglion cells (not shown) and auditory nerve 214 to the brain (also not shown) where they are perceived as sound.

Cochlear implant 200 comprises an external component 242 which is directly or indirectly attached to the body of the recipient, and an internal component 244 which is temporarily or permanently implanted in the recipient. External component 242 typically comprises one or more sound input elements, such as microphone 224 for detecting sound, a sound processor 226, a power circuit (not shown), and an external transmitter unit 228. External transmitter unit 228 comprises an external coil 230 and, preferably, a magnet (not shown) secured directly or indirectly to external coil 230. Sound processor 226 processes the output of microphone 224 that is positioned, in the depicted embodiment, by auricle 210 of the recipient. Sound processor 226 generates encoded signals, sometimes referred to herein as encoded data signals, which are provided to external transmitter unit 228 via a cable (not shown). Sound processor 226 may further comprise a data input interface (not shown) that may be used to connect sound processor 226 to a data source, such as a personal computer or personal music player.

Internal component 244 comprises an internal receiver unit 232, a stimulator unit 220, and a stimulating lead assembly 218. Internal receiver unit 232 comprises an internal coil 236, and preferably, a magnet (also not shown) fixed relative to the internal coil. Internal receiver unit 232 and stimulator unit 220 are hermetically sealed within a biocompatible housing, sometimes collectively referred to as a stimulator/receiver unit. The internal coil receives power and stimulation data from external coil 230. Stimulating lead assembly 218 has a proximal end connected to stimulator unit 220, and a distal end implanted in cochlea 240. Stimulating lead assembly 218 extends from stimulator unit 220 to cochlea 240 through mastoid bone 219. In some embodiments stimulating lead assembly 218 may be implanted at least in basal region 216, and sometimes further. For example, stimulating lead assembly 218 may extend towards apical end of cochlea 240, referred to as cochlea apex 234. In certain circumstances, stimulating lead assembly 218 may be inserted into cochlea 240 via a cochleostomy 222. In other circumstances, a cochleostomy may be formed through round window 221, oval window 212, the promontory 223 or through an apical turn 247 of cochlea 240.

Stimulating lead assembly 218 comprises a longitudinally aligned and distally extending array 246 of electrode contacts 248, sometimes referred to as array of electrode contacts 246 herein. Although array of electrode contacts 246 may be disposed on stimulating lead assembly 218, in most practical applications, array of electrode contacts 246 is integrated into stimulating lead assembly 218. As such, array of electrode contacts 246 is referred to herein as being disposed in stimulating lead assembly 218. Stimulator unit 220 generates stimulation signals which are applied by electrode contacts 248 to cochlea 240, thereby stimulating auditory nerve 214. Because, in cochlear implant system 200, stimulating lead assembly 218 provides stimulation, stimulating lead assembly 218 is sometimes referred to as a stimulating lead assembly.

In cochlear implant system 200, external coil 230 transmits electrical signals (that is, power and stimulation data) to internal coil 236 via a radio frequency (RF) link. Internal coil 236 is typically a wire antenna coil comprised of multiple turns of electrically insulated single-strand or multi-strand platinum or gold wire. The electrical insulation of internal coil 236 is provided by a flexible silicone molding (not shown). In use, implantable receiver unit 232 may be positioned in a recess of the temporal bone adjacent auricle 210 of the recipient.

As used herein, the term hearing aid refers to an electroacoustic device configured to improve sound perception. Exemplary types of hearing aids include, body worn aids, behind the ear (BTE) aids, in the ear (ITE) aids, Receiver in the Canal/Ear (CRT/RIC/RITE) aids, in the canal (ITC) aids, mini canal (MIC) aids, completely in the canal (CIC) aids, invisible in canal (IIC) aids, bone conduction devices, etc.

Figure 4:
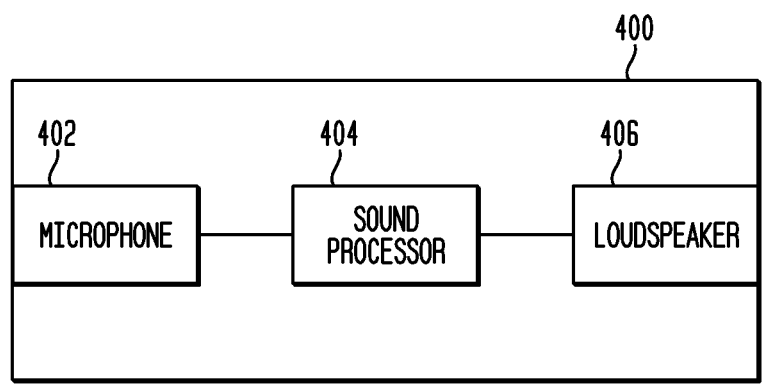
FIG. 4 is simplified functional block diagram of an exemplary hearing aid, in accordance with an embodiment of the present invention.

FIG. 4 is simplified functional block diagram of an exemplary hearing aid 400 that may be used as hearing aid 104 of FIG. 1. As illustrated, hearing aid 400 comprises a microphone 402, a sound processor 404, and a loudspeaker 406. Each of these components may be similar to components currently used in standard hearing aids. For simplicity, other components, such as an ear mold, tubes, etc., are not illustrated.

Although the presently discussed embodiment is discussed with reference to a behind the ear (BTE) hearing aid being worn by the recipient, in other embodiments, the recipient may be fitted with other types of hearing aids (e.g., a bone conduction device) or a middle or inner ear mechanical stimulation system. Or, for example, in another embodiment, the recipient is fitted only with a cochlear implant in one ear and the opposite ear uses natural hearing (i.e., a cochlear implant is attached to one ear and no hearing device is attached to the opposite ear).

Figure 5:
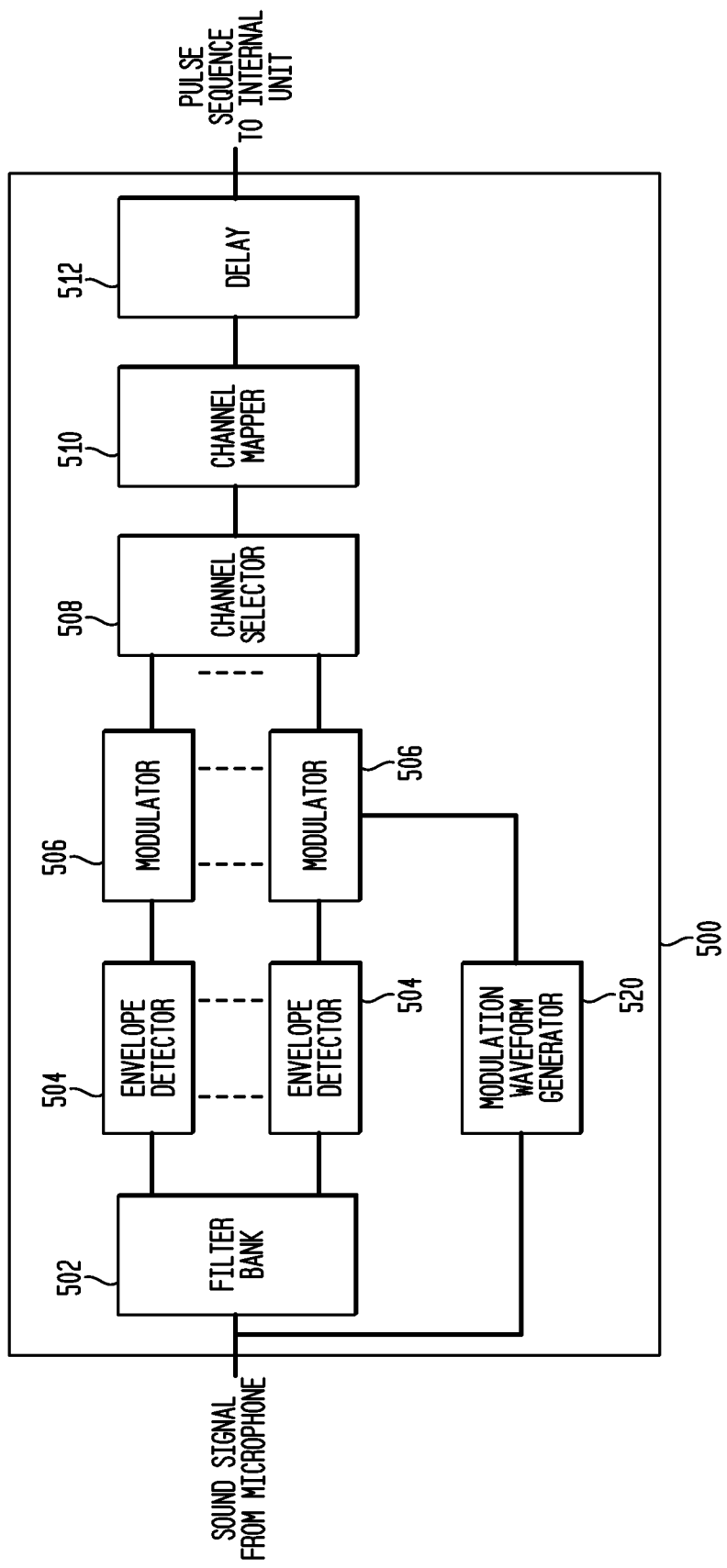
FIG. 5 provides a functional block diagram of a sound processor, in accordance with an embodiment of the present invention

FIG. 5 provides a functional block diagram of a sound processor 500, in accordance with an embodiment of the present invention. Sound processor 500 may be used as sound processor 226 of FIGS. 2 and 3. As shown, sound processor 500 comprises a filter bank 502, a plurality of envelope detectors 504, a plurality of modulators 506, a channel selector 508, a channel mapper 510, and a modulation waveform generator 520. Although not illustrated, in an embodiment, the sound processor 500 comprises circuitry and/or software for preprocessing the signal. In an embodiment, this includes one or more of a pre-emphasis filter, automatic gain control (AGC), and/or manual sensitivity control (MSC), and other signal pre-processing components. The structure and operation of audio-preprocessing is considered to be well-known in the art and, therefore, is not described further herein.

As illustrated, an electronic sound signal (e.g., from microphone 224) is received by sound processor 500 and provided to filter bank 502. In an embodiment, filter bank 502 is a Fast Fourier Transform (FFT) filter bank and processes the received sound signal to obtain a plurality of band-pass filtered frequency channel signals (e.g., 22 frequency channel signals). For example, in an embodiment, FFT filter bank executes an FFT that operates at a fixed analysis rate and a specified overlap rate to generate a plurality of frequency bin outputs. In an embodiment, the FFT is a 128 point FFT with a sample rate of 16 kHz. FFT filter bank 502 then combines these samples to obtain the plurality of frequency channel signals. Further, in other embodiments, the filter bank may be a bank of infinite impulse response (IIR) or finite impulse response (FIR) filters.

In an embodiment, envelope detectors 504 detect the envelope of each of the frequency channel signals output by FFT filter bank 502 In an embodiment, envelope detectors 504 are Hilbert envelope detectors. Envelope detector 504, in an embodiment, further includes a low-pass filter (LPF) set to a specified cut-off frequency. In an embodiment, the LPF filters the envelopes with an $8^{th}$ order Butterworth low-pass filter with a cut-off frequency of 80 Hz.

In addition to the sound signal being provided to FFT filter bank 502, the sound signal is also provided to modulation waveform generator 520. Modulation waveform generator 520 determines the timing at which modulation will be applied by modulators 506, discussed below. Further, modulation waveform generator 520 may generate the modulation waveforms to be used at the specified timing, as discussed further below.

In an embodiment, modulation waveform generator 520 identifies amplitude inflections (i.e., peaks or troughs) in the received sound signal, and the timing of the identified inflections is the determined timing for the application of modulation by modulator 506. In an embodiment, the identified inflections (i.e., peaks or troughs) represent the most energetic portions of the signal over a particular time period (e.g., the time period prior to the inflection having a length equal to the expected fundamental period of the signal). These time instances may be identified based on the absolute value of the inflection having an intensity that is greater than a particular percentage (e.g., 50% greater) of the average intensity of the signal over the time period. In an embodiment, the identified inflection is the first peak in a series of peaks that has an intensity greater than the particular percentage above the average intensity. For explanatory purposes, the inflections identified in the below discussed embodiments are peaks. However, in other embodiments, troughs may be identified and used for determining the timing for the application of modulation.

Various mechanisms may be used for identifying peaks in the received sound signal. In an embodiment, modulation waveform generator 520 determines the time instants at which the glottis closes during a voiced utterance. This time instant corresponds to a peak in the resulting sound pressure level that is repeated with a particular period.

Figure 6:
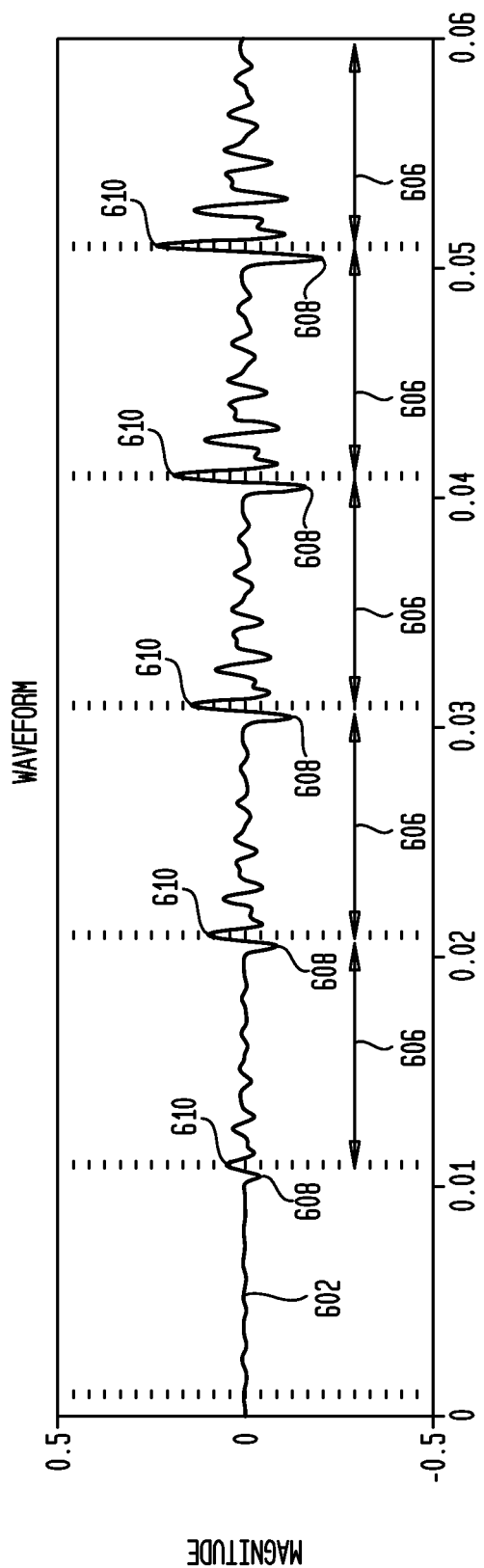
FIG. 6 illustrates an exemplary received sound signal.

FIG. 6 illustrates an exemplary received sound signal 602 and will be used to describe the concept of detecting peaks in the received sound signal. As illustrated, sound signal 602 comprises a plurality of modulations 606 that are periodically repeated, although with different levels of intensity (i.e., amplitudes). Each of these modulations is preceded by a trough 608 followed by a peak 610 at the start of the modulation and then the amplitudes of subsequent peaks in the modulation 606 decrease until the next trough 608 followed by a peak 610 occurs. In an embodiment, modulation waveform generator 520 detects the peaks 610. In one such embodiment, this is done by determining the fundamental frequency using an autocorrelation-based method and finding a local extremum based on the found fundamental frequency.

In another embodiment, modulation waveform generator 520 determines the envelope of the received sound signal (e.g., prior to filter bank 502). Modulation waveform generator 520 then selects the peak of the envelope. Modulation waveform generator 520 then provides the timing of the envelope peaks to modulators 506, which applies the modulation(s) at the provided timing.

In another embodiment, block 520 determines the envelope of the received sound signal, and sends it to block 506 to be directly used to modulate the signals as discussed below. In a variation of this embodiment, the envelope is further enhanced before sending it to block 506, e.g., by increasing the modulation depth or sending it through a non-linear function.

Or, in another example, rather than detecting the envelope for the whole signal and determining the timing of the modulation(s) based on the envelope of the whole signal, modulation waveform generator 520 instead detects an envelope for only part of the received sound signal. For example, in an embodiment, modulation waveform generator 520 low pass filters the received signal so that the detected envelope is only for a specified range of lower frequencies of the signal, and then selects the peaks of the resulting envelope as the times for application of modulation by modulators 506. This frequency range may correspond to the frequency range that can be perceived at the acoustically stimulated ear. Or, for example, in an embodiment, modulation waveform generator 520 identifies peaks of one of the envelopes output from one of the envelope detectors 504 (e.g., the envelope for the lowest frequency channel) and uses these peaks for the timing of the applied modulation(s).

In yet another embodiment, modulation waveform generator 520 determines the timing the modulation to be applied by determining the onset of a speech utterance. Modulation waveform generator 520 may employ various mechanisms for detecting the onset of a speech utterance.

The identified time instants from the modulation waveform generator 520 and the envelope signals from envelope detectors 504 are provided to modulators 506. In an embodiment, modulators 506 multiply the corresponding low-pass filtered envelope signal by a modulation waveform specified by the modulation waveform generator 520 at the specified time instance. In an embodiment, the specified modulation waveform is common for each of modulators 506. For example, in an embodiment, the specified modulation waveform comprises a pre-defined modulation shape at each determined time instant (i.e., the time instants provided by modulation waveform generator 520) and zeros in between. In an embodiment, the predefined waveform shape for the specified modulation waveform is an exponential decay function with a magnitude that decreases from 1 to 0.25 during the first 2 milli-seconds. This waveform shape provides a steep onset slope and a relatively long dead time to help optimize Interaural Time Difference (ITD) perception.

Although in the presently discussed embodiment, the pre-defined modulation shape is an exponential shape, in other embodiments other modulation shapes may be used. For example, in embodiments, the pre-defined modulation shape may be, for example, a rectified sinusoid, a raised sinusoid, or a single pulse. As used herein, a raised sinusoid refers to a sinusoid whose minimum value is >=0, such as a sinusoid with values between 0 and 1 (e.g., $f(x)=(1+\sin(x))/2$).

In another embodiment, rather than multiplying the envelopes from envelope detectors 506 with a predefined modulation shape, the modulators 506 may modulate the envelopes from envelope detectors 504 by an envelope of the received broadband signal (i.e., prior to filtering by filter bank 502). For example, as discussed above, in an embodiment the modulation waveform generator may determine an envelope of the received signal and provided this envelop to modulators 506 for use as the modulation shape used by modulators 506.

Although the presently discussed embodiment implements a modulator 506 on each frequency channel, in other embodiments, modulators 506 may only be implemented on a subset of the frequency channels (e.g., a specified number of lower frequency channels). Alternatively, modulators 506 may mix the unmodulated and modulated signal with mixing factors that vary per channel.

Further, in an embodiment, sound processor 500 includes a component (not shown) that analyzes the sound signal to determine the probability that the received sound is voiced or unvoiced. This probability is provided to modulators 506, which then apply or don't apply modulation based on the estimate of the probability that the currently analyzed sound signal comprises a voiced signal (i.e., the sound comprises sound from a vocal cord vibration). Thus, modulators 506, in such an embodiment, apply modulation, as discussed above, if the probability the sound is voiced exceeds (or is equal to) a specified threshold (e.g., 50%), and do not apply modulation if the probability the sound is voiced is below the threshold (e.g., 50%). Alternatively, the modulators 506 could mix the unmodulated and modulated signal with a mixing factor derived from the probability of voicing.

The modulated signals are then provided to channel selector 508, which selects a specified number of frequency channels from the provided signals. In a simple example, channel selector 508 selects the modulated signals with the highest amplitudes in each frame. These selected channels are often referred to as maxima. In an embodiment, channel selectors 508 selects 8 maxima (i.e., the 8 channels with the highest amplitudes).

In another embodiment, channel selector 508 assigns a selection probability function (SPF) to each channel. Channel selector 508 then multiplies each modulated signal with its corresponding SPF to provide an adjusted modulated signal. Channel selector 508 then selects a predetermined number of the frequency channels by selecting channels whose adjusted modulated signals have the highest amplitudes. For example, in an embodiment, channel selector 508 selects 8 channels by identifying the 8 adjusted modulated signals with the highest amplitudes. This mechanism is similar to the above-discussed example of selecting maxima, but instead selects the maximum valued adjusted modulated signals. It should be noted that in this embodiment the product of the SPF and modulated signal is only used to select channels for stimulation. The signals sent to 510 Channel Mapper are not multiplied by the SPF.

Further, in an embodiment, rather than selecting a plurality of maxima, the channel selector 508 instead selects only the frequency channel with the highest amplitude (i.e., only a single frequency channel is selected). In such an embodiment, the speech processor 500 may operate at a higher frame rate (e.g., a frame rate of 14400 Hz, yielding a period of 69 μs) as opposed to a frame rate 900 Hz that may be used when a plurality of maxima (e.g., 8) are selected. In embodiments in which only 1 frequency channel is selected, there may be an extra constraint that the unweighted magnitude should be amongst the plurality (e.g. 8) of maxima.

In an embodiment, channel selector 508 resets the SPF for a particular channel each time the channel is stimulated. Channel selector 508 adjusts the SPF or leaves the SPF the same for unselected channels. For example, in an embodiment, if a frequency channel is selected, the SPF for the frequency channel in an embodiment is set to 0 for the next frame, and thus the channel will not be selected in the next frame (i.e., the next frame of signals output by FFT filter bank 502 and subsequently modulated by modulators 506). The SPF for the frequency channel then remains at 0, for a specified number of frames (e.g., 4 frames) and then is set to 1 until the frequency channel is selected again.

In yet another embodiment, the SPF may be determined based on a function of the excitability of neurons in the vicinity of at least one electrode corresponding to the frequency channel. This function may be based on an auditory neuron recovery function and depend on not just stimulation applied on the frequency channel but also stimulations applied on other frequency channel (e.g., neighboring frequency channels) such as discussed in U.S. Patent Publication No. 2011-0077712, entitled "Sound Processing Method and System," by Matthijs Killian, which is hereby incorporated by reference herein.

The selected modulated frequency channel signals are provided by the channel selector 508 to the channel mapper 510, which maps the received signals to current levels. For example, in an embodiment, each signal from blocks 502-508 may be in units ranging from a value 0 to 1. Channel mapper 510, in an embodiment, converts the magnitude, M, of the frequency channel signal to current level using the following formula: $CL = V*M*(C-T)+T$, where CL is the Current Level, M is the magnitude of the frequency channel signal, C is the maximum comfort level for the frequency channel, T is the threshold level for the frequency channel, and V is the volume. In an embodiment, the volume, V, is fixed at 1. In an embodiment, the current level may be determined using a loudness growth function, such as is known to those of skill in the art. However, in other embodiments, the volume is adjustable by the audiologist and/or recipient between a specified range, such as, for example, between 0.8 and 1.0.

As noted above, in an embodiment, the signals provided to the left ear and the right ear of the recipient are synchronized for signals arriving from directly in front of the listener. As illustrated, the determined current level signal from current mapper 510 are provided to a delay 512 that may delay the signal. Similarly, the processor (e.g., sound processor 404 of FIG. 4) for the opposite ear may also include a delay function that may delay the application of stimulation from the device on the opposite ear so that the signals provide to both ears are synchronized for signals arriving from directly in front of the listener. In other words, the delays are equalized on each side so that the delay between when sound arrives at the respective microphone and stimulation is applied to the auditory nerve is the same for both sides. For example, in embodiments, a delay may be imposed by the hearing aid using the following formula: $D_{AHA} = D_{CI} - D_{HA} - D_{travelling\ wave}$, where $D_{AHA}$ is the delay applied by the hearing aid, $D_{CI}$ is the processing delay of the cochlear implant, $D_{HA}$ is the processing delay of the hearing aid and $D_{travelling\ wave}$ is the traveling wave delay in the acoustic path. In an embodiment, the signal is only delayed on one side of the recipient to synchronize the signals. For example, if $D_{AHA}$ is less than 0, then a delay is applied by the cochlear implant, but not the hearing aid; or if $D_{AHA}$ is greater than 0, then a delay is applied by the hearing aid but not the cochlear implant.

On the opposite ear of the recipient (i.e., the side fitted with, for example, a hearing aid) the sound applied to the recipient traverses an acoustic path in which the stimulus is subject to traveling wave delay. For ease of explanation, the device on the opposite ear of the recipient will be assumed to be a hearing aid, such as illustrated in FIG. 1. Traveling wave delay is not present in the electrical stimulation path (e.g., the side fitted with a cochlear implant). Therefore, without the cochlear implant applying a delay, the stimulation applied by the cochlear implant may be provided sooner than the corresponding stimulation applied by the hearing aid or natural hearing. This lack of synchronization results in the perceived ITD being incorrect, which can result in localization errors.

In an embodiment, delay 512 applies a delay in the electrical stimulation path to compensate for the acoustic traveling wave delay in the opposite ear's acoustic path. In such a manner, the time lag between arrival of a sound signal at the recipient's ear and stimulation of the corresponding auditory nerve is the same for both ears (e.g., through electrical stimulation by the cochlear implant and through acoustic stimulation to the opposite ear). As used herein, application of acoustic stimulation refers to stimulation of the auditory nerve as a consequence of the activation of the hair cells due to a sound signal (e.g., an amplified sound signal generated by a hearing aid). In an embodiment, the delay applied by delay 512 is a constant delay. This delay may be calculated for the particular recipient, or, for example, a delay based on average psychophysical data (e.g., 1.5 milliseconds).

The applied delay may be constant across all frequency channels, or frequency channel dependent, to take into account the frequency dependence of the traveling wave delay in the acoustically stimulated ear. In an embodiment, the internal clocks of the cochlear implant and hearing aid (or other device fitted to the opposite ear) are synchronized using for example, a wired or wireless connection. Synchronization of the internal clocks may help preserve the interaural timing cues.

Although FIG. 5 illustrates delay 512 on the right side of the sound processor 500, it should be understood that in other embodiments the delay may be applied at different points along the processing path, such as, for example, prior to filtering the signal by filter bank 502.

The following provides a description of an exemplary method for calculating a delay for delay 512. In this example, it is assumed that the difference in delay is dominated by the traveling wave delay in the acoustic path on the hearing aid side of the recipient. Thus, in this example, a delay is applied by the cochlear implant, but not the hearing aid of the recipient. The method of this embodiment is based on the extent of lateralization of sound perceived by the recipient. That is, if the perceived sound can be steered equally far to either side of the recipient's head by varying only the ITD, the sound is considered balanced and level.

Initially, the cochlear implant and hearing aid are each connected to a fitting system. The fitting system may be, for example, a computer or specialized piece of hardware that executes software for use in performing the method. Further, it is assumed that cochlear implant and hearing aid have been individually (mononaurally) fitted prior to commencement of this procedure. That is, a cochlear implant is attached to one ear of the recipient and a hearing aid is attached to the other ear in the presently described embodiment.

The fitting system presents a binaural sound signal to each of cochlear implant and the hearing aid to center the sound image. This initial sound is presented to the cochlear implant and hearing aid simultaneously. The fitting system, in the present embodiment, provides this signal directly to the sound processors of the cochlear implant and hearing aid (e.g., sound processor 126 and 404, respectively), bypassing the microphone. As a starting point, a population average delay (e.g., 1.5 milli-seconds) is chosen for delaying the sound provided to the cochlear implant. The fitting system then adjusts the intensity of the sound signal presented to the devices for each ear until the recipient indicates that the sound image is centered (i.e., the sound is perceived as being centered between the recipient's ears).

The fitting system then, increases a delay in the signal presented to the cochlear implant, such that the sound signal is first presented to the hearing aid and then, after the delay, is presented to the cochlear implant. This delay is designed to mimic an ITD, and is increased until the sound is perceived as originating on the side of the hearing aid (i.e., at a direction 90 degrees from the forward direction of the recipient). If the sound cannot be steered to the hearing aid side, the level balance is adjusted (by relatively increasing the level at the hearing-aid side).

Once the sound is perceived as originating on the side of the hearing aid, the fitting system sets the delay of the signal presented to the cochlear implant at 0, and sets the delay of the sound signal presented to the hearing aid to at least the final used delay (i.e., the delay to the CI that achieved the maximal extent of laterality). If this sound is perceived as originating on the cochlear implant side (i.e., at a direction 90 degrees from the forward direction of the recipient), the level balance is considered correct and the traveling wave delay is measured.

If, however, the percept cannot be steered equally far to either side of the head, the level balance is adjusted (by relatively increasing the level at the CI side) and the process is repeated.

Figure 7:
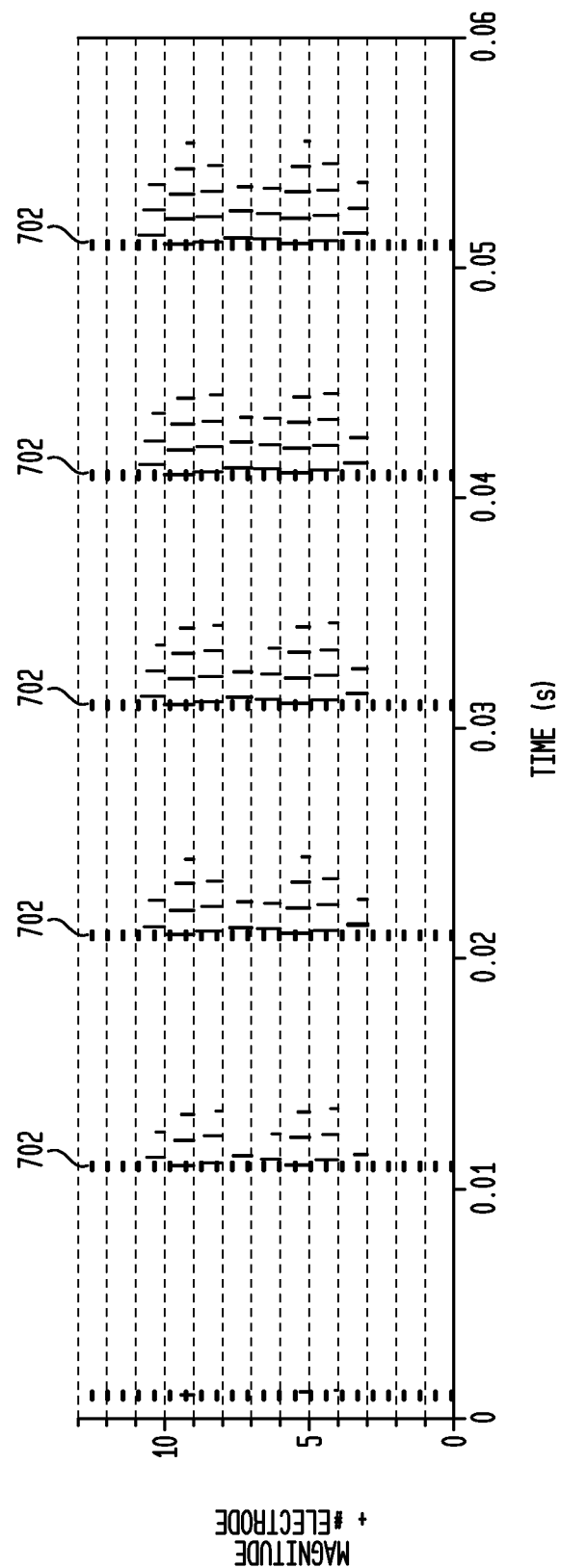
FIG. 7 illustrates an electrodogram that illustrates stimulation pulses, in accordance with an embodiment of the present invention.

Once the correct level balance is obtained, the traveling wave delay is determined by determining the delay that yields a sound image that is perfectly centered, e.g., by presenting a large range of delays and selecting the one that yields the most centered percept, or by varying the delay in a way such as to converge to the delay that leads to a centered percept FIG. 7 illustrates an electrodogram that illustrates stimulation pulses, in accordance with an embodiment of the present invention. The stimulation pulses of FIG. 7 are exemplary stimulation pulses for a system such as discussed above with reference to FIG. 5. The vertical, dashed lines 702 represent GCIs determined for the input sound signal of FIG. 6. The determined stimulation pulses are illustrated as solid vertical lines along the line representative of a particular electrode. As shown, in this example, the stimulations for 14 electrodes (the 14 lowest frequency electrodes) are illustrated, where each electrode corresponds to a particular frequency channel. Further, in this example, the pre-defined modulation shapes applied by modulators 506 are exponential decay functions, such as discussed above. Further, in this example, channel selector 508 uses the SPF mechanism described above and additionally restricts stimulation to the 8 highest amplitude frequency channels for application of stimulation.

As shown, in this example, the stimulation pulses on the selected frequency channels are applied beginning at the time of the identified GCI, which in the illustrated example occur with a period of approximately 0.01 seconds. These pulses then exponentially decay to zero within approximately 0.004 seconds.

Figure 8:
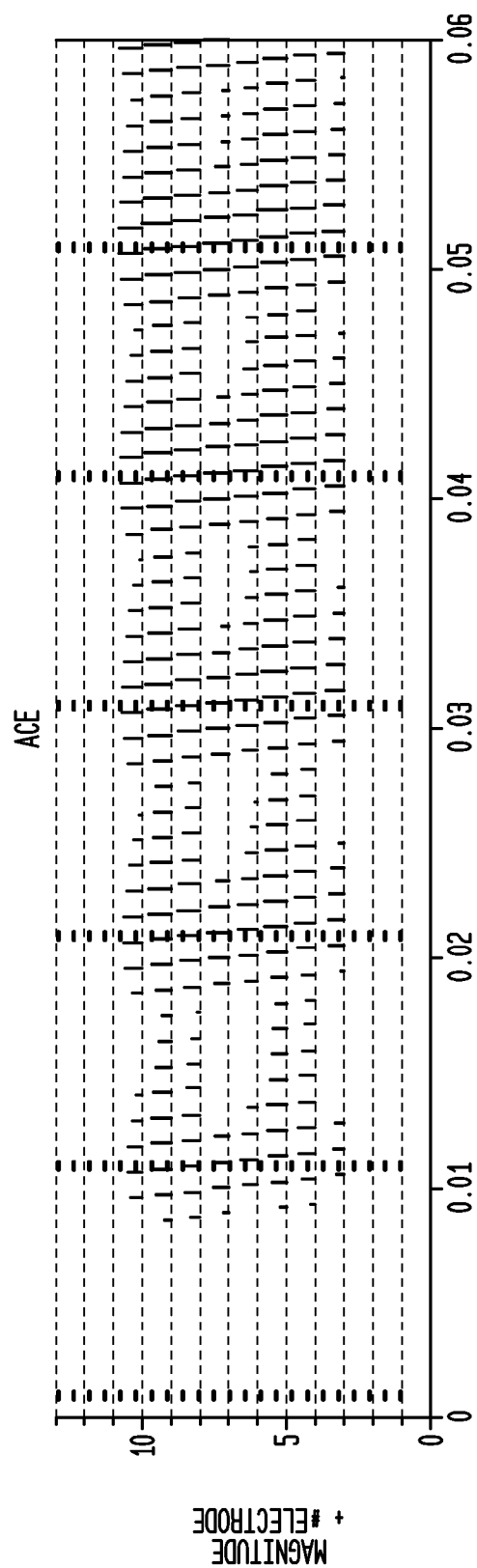
FIG. 8 illustrates an electrodogram that illustrates stimulation pulses for an Advanced Combination Encoder (ACE) strategy.

FIG. 8 illustrates an electrodogram that illustrates stimulation pulses for an Advanced Combination Encoder (ACE) strategy. FIG. 8 is provided for comparison purposes with the electrodogram of FIG. 7. As shown in FIG. 8, the stimulation pulses are more evenly spaced throughout the time period between GCIs and for many frequency channels, the stimulation pulses are evenly distributed throughout the entire time period between the GCIs for the received sound signal.

In addition to employing a strategy, such as discussed above, that is implemented in the cochlear implant, in an embodiment, the hearing aid (or other device fitted to the recipient's ear opposite the cochlear implant) may also employ strategies that may enhance ITD perception. For example, in an embodiment, the hearing aid may low pass filter the received sound signal so that only frequencies below a specified frequency are amplified by the hearing aid. Or, for example, in an embodiment, the sound processor of the hearing aid implements a mechanism that increases the modulation depth of the sound signal amplified by the hearing aid (or other device). Or, for example, the sound processor of the hearing aid (or other device) implements a mechanism that shifts the fundamental frequency, F0, of the sound signal. In such an embodiment, the sound processor may implement, for example, the pitch synchronous overlap add method (PSOLA).

Further, in an embodiment, the sound processor of the hearing aid (or other device) compresses the frequency range of the sound signal. Or, in yet another embodiment, the hearing aid (or other device) implements a mechanism that selects the fundamental frequency, F0, and then imposes the fundamental frequency, F0, on a tone that is conveyed to the recipient. It should be noted that the hearing aid (or other device), in embodiments, may combine one or more of these techniques to help enhance ITD perception.

In addition to providing improved ITD perception, the above-discussed embodiments may also offer improved F0 or music perception, improved perceptual fusion between modalities and improved speech understanding in noise due to binaural unmasking.

Although the above discussed embodiments were principally discussed with reference to a cochlear implant fit to one ear and a hearing aid to the other ear, in other implementations embodiments of the present invention may be employed in other hearing systems. For example, an embodiment may be employed in hybrid systems, such as when a hybrid system comprising a cochlear implant and hearing aid is fit to one ear of the recipient. Or, for example, embodiments may be employed in bilateral hybrid systems, bilateral cochlear implant systems, or even a mononaural hybrid system.

Various implementations of the subject matter described, such as the embodiment of FIG. 5 (including the illustrated functional blocks) may be realized in digital electronic circuitry, integrated circuitry, specially designed ASICs (application specific integrated circuits), computer hardware, firmware, software, and/or combinations thereof. These various implementations may include one or more computer programs that are executable and/or interpretable on a programmable system including at least one programmable processor, which may be special or general purpose.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, the exemplary implementations described herein (e.g., the embodiment of FIG. 5) may include a processor and a memory coupled to the processor. The memory may include one or more programs that cause the processor to perform one or more of the operations (e.g., one or more of the functional blocks illustrated in FIG. 5) described herein.

It is to be understood that the detailed description and specific examples, while indicating embodiments of the present invention, are given by way of illustration and not limitation. Many changes and modifications within the scope of the present invention may be made without departing from the spirit thereof, and the invention includes all such modifications. Further, reference herein to "one embodiment" or "an embodiment" means that a particular feature, structure, operation, or other characteristic described in connection with the embodiment may be included in at least one implementation of the invention. However, the appearance of the phrase "in one embodiment" or "in an embodiment" in various places in the specification does not necessarily refer to the same embodiment. It is further envisioned that a skilled person could use any or all of the above embodiments in any compatible combination or permutation.

What is claimed is:

1. A method for delivering an electrical stimulation signal by a hearing device having a plurality of electrodes, the method-comprising:
    receiving a sound signal at the hearing device;
    filtering the sound signal to obtain a first set of one or more band-pass filtered signals;
    determining a time instance of an amplitude inflection in the sound signal; and
    modulating at least one of the band-pass filtered signals with a pre-defined modulation shape at the determined time instance;
    delivering, via one or more of the plurality of electrodes, a stimulation signal using the modulated at least one band-pass filtered signal and a traveling wave delay.

2. The method of claim 1, wherein determining the time instance of the amplitude inflection in the sound signal comprises:
    determining the time instance based on an absolute value of a selected amplitude inflection having an intensity that is greater than a particular percentage of an average intensity of the sound signal over a particular time period.

3. The method of claim 2, wherein the selected amplitude inflection is indicative of a glottal closure instant.

4. The method of claim 2, wherein the selected amplitude inflection is indicative of a fundamental frequency of the sound signal.

5. The method of claim 2, wherein the selected amplitude inflection is indicative of the onset of an utterance.

6. The method of claim 2, wherein determining a time instance comprises:
    determining an envelope of the sound signal; and
    determining the time instance based on a peak of the determined envelope.

7. The method of claim 1, further comprising:
    determining an envelope of the at least one band-pass filtered signal; and
    wherein modulating the at least one band-pass filtered signal at the determined time instance, comprises:
    multiplying the envelope of the at least one band-pass filtered signal with the pre-defined modulating shape.

8. The method of claim 7, wherein the pre-defined modulating shape is selected from the set of:
    a rectified sinusoid, a raised sinusoid, and an exponential decay function.

9. The method of claim 1, wherein modulating at least one of the band-pass filtered signals at the determined time instance comprises: modulating a plurality of band-pass filtered signals to generate a plurality of modulated band-pass filtered signals; and wherein the method further comprises:
    selecting a subset of the plurality of modulated band-pass filtered signals; and
    wherein delivering the stimulation signal using the modulated at least one band-pass filtered signal and a traveling wave delay comprises delivering a stimulation signal for each modulated band-pass filtered signal of the subset.

10. The method of claim 9, wherein selecting a subset of the plurality of modulated band-pass filtered signals comprises:
    multiplying at least one of the plurality of modulated band-pass filtered signals by a number specified for a frequency channel corresponding to the at least one of the plurality of modulated band-pass filtered signals to weigh an intensity of the modulated band-pass filtered signal; and selecting a specified number of the plurality of modulated band-pass filtered signals based on the intensity of the weighted band-pass filtered signals.

11. The method of claim 10, wherein the specified number is based on a time since a previous stimulation was applied on the frequency channel.

12. The method of claim 1, wherein the hearing device is attached to a first ear of a recipient of the hearing device, and wherein a hearing aid is attached to the second ear of the recipient, and further comprising:
    wherein the traveling wave delay is determined based on a difference in a time lag between receipt of the sound signal at the first ear and electrical stimulation of the auditory nerve of the first ear by the hearing device and a time lag between receipt of the sound signal at the second ear and stimulation of the auditory nerve of the second ear by the hearing aid.

13. The method of claim 12, wherein the traveling wave delay is configured to account for a traveling wave delay in the application of acoustic stimulation to the second ear of the recipient.

14. A hearing device comprising:
    a filter bank configured to obtain a first set of one or more band-pass filtered signals from a received sound signal;
    a time selector configured to analyze the received sound signal to determine a time instance of an amplitude inflection in the received sound signal;
    at least one modulator configured to receive an indication of the determined time instance from the time selector and to modulate at least one of the band-pass filtered signals with a pre-defined modulation shape at the determined time instance to generate at least one modulated band-pass filtered signal; and
    a traveling wave delay configured to cause a delay in application of electrical stimulation in accordance with the at least one modulated band-pass filtered signal; and a plurality of electrodes configured to deliver a stimulation signal generated based on the at least one modulated band-pass filtered signal to a first ear of a recipient of the hearing device.

15. The hearing device of claim 14, wherein the time selector is configured to determine the time instance of the amplitude inflection in the received sound signal based on an absolute value of a selected amplitude inflection having an intensity that is greater than a particular percentage of an average intensity of the received sound signal over a particular time period.

16. The hearing device of claim 15, wherein the selected amplitude inflection is indicative of a glottal closure instant.

17. The hearing device of claim 15, wherein the selected amplitude inflection is indicative of a fundamental frequency of the sound signal.

18. The hearing device of claim 15, wherein the selected amplitude inflection is indicative of the onset of an utterance.

19. The hearing device of claim 15, wherein the time selector is configured to determine an envelope of the sound signal and determine the time instance based on a peak of the determined envelope.

20. The hearing device of claim 14, further comprising:
an envelope detector configured to determine an envelope of the at least one band-pass filtered signal; and
wherein to modulate at least one of the band-pass filtered signals with the pre-defined modulation shape, the at least one modulator is configured to multiply the envelope of the band-pass filtered signal with the pre-defined modulating shape at the determined time instance.

21. The hearing device of claim 20, wherein the selected modulation waveform is selected from the set of: a rectified sinusoid, a raised sinusoid, and an exponential decay function.

22. The hearing device of claim 14, wherein the at least one modulator comprises a bank of modulators each configured to multiply at least one of the one or more band-pass filtered signals by a pre-defined modulation shape at one or more determined time instances to generate a plurality of modulated band-pass filtered signals, the hearing device further comprising:
a channel selector configured to select a subset of the plurality of modulated band-pass filtered signals for use in a generating a stimulation signal for delivery to the recipient via the plurality of electrodes.

23. The hearing device of claim 22, wherein to select the subset of the plurality of modulated band-pass filtered signals, the channel selector is configured to weigh an intensity of at least one of the plurality of modulated band-pass filtered signals by a number specified for a frequency channel corresponding to the at least one of the plurality of modulated band-pass filtered signals, and select a specified number of the plurality of modulated band-pass filtered signals based on the weighted intensity of the modulated band-pass filtered signals.

24. The hearing device of claim 23, wherein the specified number is based on a time since a previous stimulation was applied on the frequency channel.

25. The hearing device of claim 14, wherein the hearing device is part of a bilateral hearing system that includes an acoustic stimulation hearing aid configured to deliver acoustic stimulation to a second ear of the recipient to evoke perception of the received sound signal at the second ear, and wherein the traveling wave delay is configured to delay delivery of the stimulation signal generated based on the at least one modulated band-pass filtered signal to the first ear of recipient via the plurality of electrodes to account for a delay in the application of the acoustic stimulation to the second ear of the recipient.

26. The hearing device of claim 14, wherein the hearing device comprises a cochlear implant.

27. A bilateral hearing system comprising:
an acoustic stimulation hearing aid configured to be attached to a first ear of a recipient and to deliver acoustic stimulation representative of a sound signal; and
an electrical stimulation hearing device configured to be attached to a second ear of the recipient, wherein the electrical stimulation hearing device comprises:
a filter bank configured to obtain a first set of one or more band-pass filtered signals from the sound signal;
a time selector configured to determine a time instance of an amplitude inflection in the sound signal;
a modulator connected to the filter bank to receive the or more band-pass filtered signals and connected to the time selector to receive an indication of the determined time instance, wherein the at least one modulator is configured to modulate at least one of the band-pass Filtered signals with a pre-defined modulation shape at the determined time instance;
a traveling wave delay module configured to delay application of electrical stimulation, generated based on the at least one modulated bandpass filtered signal, to the second ear of the recipient to account for a delay in the application of the acoustic stimulation to the first ear of the recipient.

28. The bilateral hearing system of claim 27, further comprising:
an envelope detector configured to detect an envelop of the received sound signal; and
wherein the at least one modulator is configured to modulate that at least one band-pass filtered signals at the determined time instance with the detected envelope.

29. The bilateral hearing system of claim 27, further comprising:
an envelope detector configured to detect an envelop of the received sound signal; and
wherein the at least one modulator is configured to modulate the at least one band-pass filtered signal at the determined time instance by multiplying the envelope of the at least one band-pass filtered signal with the pre-defined modulating shape.

* * * * *

UNITED STATES PATENT AND TRADEMARK OFFICE
CERTIFICATE OF CORRECTION

PATENT NO. : 9,283,376 B2
APPLICATION NO. : 13/117577
DATED : March 15, 2016
INVENTOR(S) : Jan Wouters Page 1 of 1

It is certified that error appears in the above-identified patent and that said Letters Patent is hereby corrected as shown below:

In the claims

In Col. 15, line 45, claim 22, delete the first instance of "a".

In Col. 16, line 32, claim 27, delete "Filtered" and insert --filtered-- therewith.

In Col. 16, line 36, claim 27, delete "bandpass" and insert --band-pass-- therewith.

Signed and Sealed this
Seventeenth Day of May, 2016

Michelle K. Lee
*Director of the United States Patent and Trademark Office*